US011389602B2

(12) United States Patent
Abate et al.

(10) Patent No.: US 11,389,602 B2
(45) Date of Patent: Jul. 19, 2022

(54) NEBULIZATION DEVICE FOR MEDICAL MIXTURE

(71) Applicant: Flaem Nuova S.p.A., Desenzano del Garda (IT)

(72) Inventors: Riccardo Abate, Desenzano del Garda (IT); Luigi Abate, Desenzano del Garda (IT); Mauro Bertelli, Desenzano del Garda (IT); Stefano Stefanni, Desenzano del Garda (IT)

(73) Assignee: FLAEM NUOVA S.P.A., Desenzano del Garda (IT)

( * ) Notice: Subject to any disclaimer, the term of this patent is extended or adjusted under 35 U.S.C. 154(b) by 306 days.

(21) Appl. No.: 16/632,708

(22) PCT Filed: Jul. 18, 2018

(86) PCT No.: PCT/EP2018/069492
§ 371 (c)(1),
(2) Date: Jan. 21, 2020

(87) PCT Pub. No.: WO2019/016257
PCT Pub. Date: Jan. 24, 2019

(65) Prior Publication Data
US 2021/0162142 A1 Jun. 3, 2021

(30) Foreign Application Priority Data
Jul. 19, 2017 (IT) .................. 102017000082273

(51) Int. Cl.
*A61M 11/00* (2006.01)
*A61M 15/00* (2006.01)
(Continued)

(52) U.S. Cl.
CPC ........... *A61M 11/02* (2013.01); *A61M 11/001* (2014.02); *A61M 11/06* (2013.01);
(Continued)

(58) Field of Classification Search
CPC .............. A61M 11/02; A61M 15/0013; A61M 15/0018; A61M 15/002; A61M 15/0021;
(Continued)

(56) References Cited

U.S. PATENT DOCUMENTS 2,772,117 A * 11/1956 Ritzau ..................... B05B 5/025
239/135
3,658,059 A * 4/1972 Steil ..................... A61M 11/002
128/200.21
(Continued)

FOREIGN PATENT DOCUMENTS

EP 2703030 A2 3/2014
EP 2952219 A1 12/2015
(Continued)

OTHER PUBLICATIONS

International Search Report dated Sep. 3, 2018 in connection with PCT/EP2018/069492.
(Continued)

*Primary Examiner* — Tu A Vo
(74) *Attorney, Agent, or Firm* — Akerman LLP

(57) ABSTRACT

The invention relates to a nebulization device (1) for medical mixture. It comprises a containing ampoule (2) for medical mixture, comprising an upper component (2a) and a lower component (2b) connected to each other, at least one emission opening (11) of the nebulized medical mixture from the ampoule (2), and at least one entry window (19) for the intake of air within the ampoule (2). Moreover, the nebulization device (1) comprises at least one atomizer (14) for the intake of pressurized gas, within the lower component (2b) of the ampoule (2), the atomizer (14) being surmounted by the upper component (2a). Advantageously, at least one, preferably two selection side windows (24) are provided on the upper component (2a), the opening of the (Continued)

selection side windows (24) being shielded by shielding means (16), moved by a command shaft (17).

13 Claims, 9 Drawing Sheets

(51) Int. Cl.
*A61M 11/02* (2006.01)
*A61M 11/06* (2006.01)
(52) U.S. Cl.
CPC ...... *A61M 15/002* (2014.02); *A61M 15/0013* (2014.02); *A61M 15/0015* (2014.02); *A61M 15/0018* (2014.02); *A61M 15/0021* (2014.02); *A61M 11/002* (2014.02)
(58) Field of Classification Search
CPC .............. A61M 11/002; A61M 11/001; A61M 15/0015; A61M 11/06; A61M 15/009; A61M 15/0091; B05B 1/265; B05B 7/0012; B05B 7/1272; B05B 7/2435
See application file for complete search history.

(56) References Cited

U.S. PATENT DOCUMENTS

| | | | | |
|---|---|---|---|---|
| 4,886,055 A * | 12/1989 | Hoppough | ........... | A61M 16/125 128/200.14 |
| 4,976,259 A * | 12/1990 | Higson | ............. | A61M 15/0085 128/200.14 |
| 5,054,477 A * | 10/1991 | Terada | ................ | A61M 16/125 128/200.14 |
| 5,584,285 A | 12/1996 | Salter et al. | | |
| 5,687,912 A * | 11/1997 | Denyer | ................. | A61M 11/06 128/200.21 |
| 6,044,841 A * | 4/2000 | Verdun | ................. | A61M 11/06 128/200.18 |
| 6,085,741 A * | 7/2000 | Becker | ................ | A61M 11/06 128/200.21 |
| 2009/0071470 A1 * | 3/2009 | Abrams | ............ | A61M 15/0031 128/200.22 |
| 2009/0071473 A1 * | 3/2009 | Abrams | ............ | A61M 15/0038 128/203.12 |
| 2009/0133692 A1 * | 5/2009 | Abrams | ............ | A61M 15/0038 128/200.21 |
| 2009/0151716 A1 * | 6/2009 | Abrams | ............ | A61M 15/0041 128/200.14 |
| 2011/0114090 A1 * | 5/2011 | Piper | ................ | A61M 15/0021 128/200.23 |
| 2011/0253134 A1 * | 10/2011 | Chen | ....................... | A61M 11/06 128/200.23 |
| 2012/0174917 A1 * | 7/2012 | Chen | .................... | A61M 15/002 128/200.23 |
| 2012/0227735 A1 * | 9/2012 | Abate | .................... | A61M 11/06 128/200.14 |
| 2013/0327323 A1 * | 12/2013 | Rubin | ............... | A61M 16/1055 128/200.18 |
| 2014/0060526 A1 * | 3/2014 | Wang | .................. | A61M 16/201 128/200.18 |
| 2014/0116427 A1 * | 5/2014 | Pevler | ............... | A61M 16/0063 128/200.18 |
| 2014/0261401 A1 * | 9/2014 | Esaki | ..................... | A61M 11/02 128/200.21 |
| 2014/0263743 A1 * | 9/2014 | Esaki | ..................... | A61M 11/06 239/338 |

FOREIGN PATENT DOCUMENTS

| | | |
|---|---|---|
| EP | 3017839 A1 | 5/2016 |
| WO | 02/074370 A2 | 9/2002 |
| WO | 2011/045827 A1 | 4/2011 |
| WO | 2011158715 A1 | 12/2011 |

OTHER PUBLICATIONS

Written Opinion of the international Searching Authority dated Sep. 3, 2018 in connection with PCT/EP2018/069492.

* cited by examiner

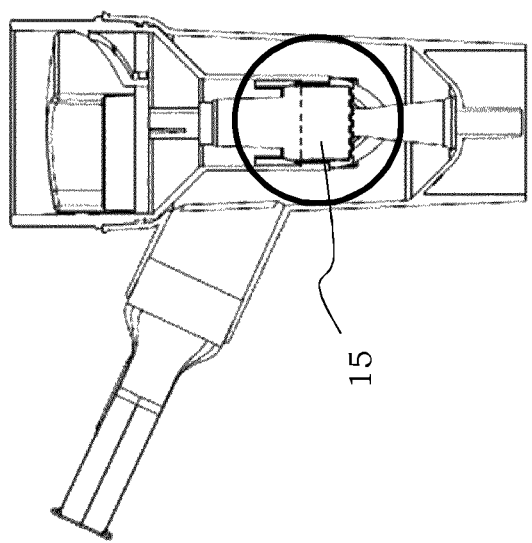
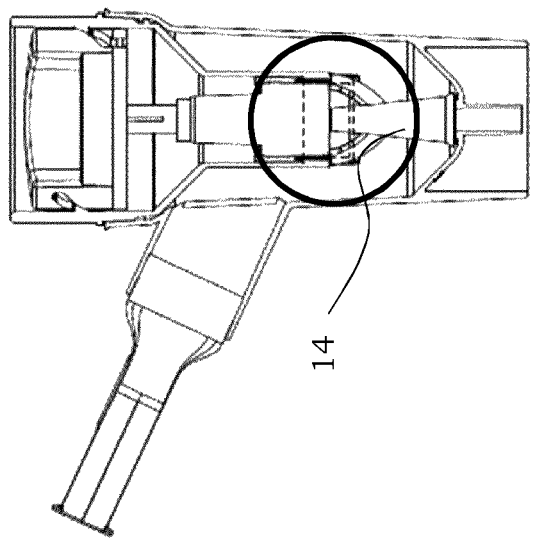
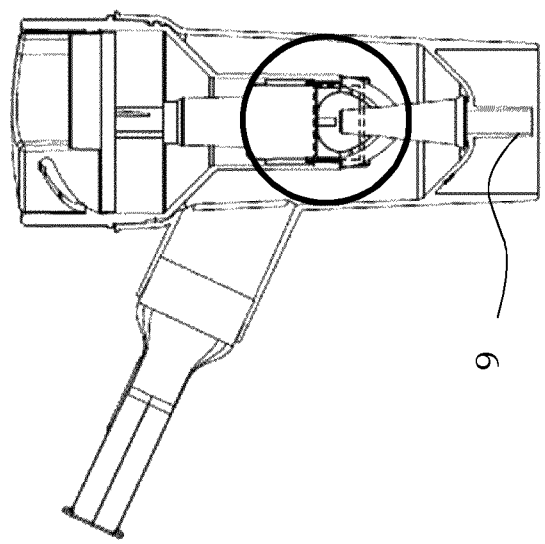
FIG. 2a POSITION 1
FIG. 2b POSITION 2
FIG. 2c POSITION 3

POSITION 1

POSITION 2

POSITION 3

NEBULIZATION DEVICE FOR MEDICAL MIXTURE

CROSS-REFERENCE TO RELATED APPLICATIONS

This application is a national phase of PCT/EP2018/069492, filed Jul. 18, 2018, and claims priority to Italian Patent Application No. 102017000082273, filed Jul. 19, 2017, the entire contents of both of which are hereby incorporated by reference.

FIELD OF APPLICATION

The present invention relates to a portable nebulization device for medical fluids, and in particular to a universal nebulization device, optimized for the treatment of all of the tracts of a patient's respiratory system.

The above nebulization apparatus finds useful application in the medical field, particularly in the aerosol therapy field.

PRIOR ART

The administration of drugs by air tract through appropriate nebulizing devices is a therapeutic practice usually employed in relation to numerous diseases, especially of the respiratory apparatus.

In particular, nebulization allows dividing a drug in the liquid form into a plurality of very fine particles, having a diameter of a few micrometers, which can be easily inhaled by a patient.

It is also known that for the treatment of the various tracts of the respiratory system a specific nebulization is necessary.

Indeed, in order for the nebulized particles to be able to reach differently the upper respiratory tract, the tracheo-bronchial tract or the pulmonary alveoli a different sizing is needed.

In fact, for a treatment involving the first respiratory tract a coarser nebulization is recommended, whereas for the deeper respiratory tracts a very fine nebulization is essential.

The optimal granulometry for the treatment of the specific respiratory tracts is indicated in the bibliography and in the specific UNI EN 13544-1 standard, which specifies that:

- a diameter greater than 5 μm allows a deposition in the upper respiratory tract;
- a diameter comprised between 2 μm and 6 μm allows a deposition in the tracheo-bronchial tract;
- a diameter comprised between 0.5 μm and 3 μm allows a deposition at the level of the pulmonary alveoli.

In order to obtain a granulometry suitable for the various needs above listed, the most adopted solution has been that of using specific components for each purpose.

In particular, within a known configuration of a nebulization device, more atomizers have been provided, from which pressurized gas is introduced (also called "pisper").

According to the adopted atomizer, there is indeed a more or less fine nebulization of the medical liquid.

This type of solution allows obtaining the undoubted advantage of providing precise dimensional atomization values for all needs.

However, it is equally clear that this solution also implies the drawback of being more difficult to be used.

In fact, it is necessary for the patient to have a minimum competence in choosing the correct atomizer in own specific case. This clearly involves the inherent risk of an incorrect choice of the atomizer.

To this drawback those of lack of practicality due to the need for replacement and to keep a greater quantity of components of the nebulization device with the risk of loss when not used are added.

For this reason, devices allowing a geometric positioning variation of the same components to obtain a different nebulization have also been provided.

For instance, European patent application no. EP 2 952 219 A1 to 3A Health Care S.r.l. provides for a displacement of the air intake duct within the nebulization device, in order to vary the relative position thereof with respect to the atomizer from which pressurized gas is introduced.

Although this solution allows an advantage for the different nebulization obtained based on the relative position between the two above mentioned components, it also has drawbacks from an operation point of view.

In fact, due to the structural complexity, it does not allow a correct disassembling among the nebulization device components and a consequent inadequate cleaning/disinfection/sterilization.

In fact, we wish torecall that, since the nebulization devices are used for patients suffering from lung infections, all the components adopted must ensure a certain level of sterilization, so as not to further worsen said infection.

Another known technical solution is disclosed in U.S. Pat. No. 3,658,059 A, which relates to an inhaler provided with a diaphragm to change the effective size of the passage suitable for making the suspension to be inhaled pass. The diaphragm is moved towards and away from the inhaler jet, in order to increase or reduce the opening. Though advantageous under various aspects, this solution does not allow a simple disassembling of the components to favour the cleaning and sterilization thereof.

A further known solution is described in European patent application no. EP 3 017 839 A1, which relates to a device for aerosol nebulizing substances with a separation element configured to divide the nebulization chamber into at least two sectors and with means for moving the separation element and adjusting the flow rate exiting from the device. This solution as well is not effective from the point of view of simplicity and ease of use in adjusting the nebulization level of the medicament by the user.

An object of the present invention is to provide a nebulization device that allows obtaining a different granulometry of the particles according to the needs of the specific patient, without replacing the components.

A further object is to provide the total disassembling of the nebulization device to allow the correct cleaning/disinfection/sterilization of the adopted components.

Another object is to provide a nebulization device of practical use, even by not particularly experienced patients.

Finally, a further object is to provide a nebulization device that is structurally simple so as to avoid constructive problems which are not suitable for a product intended for mass production.

SUMMARY OF THE INVENTION

The solution idea underlying the present invention is to provide a nebulization device that allows the intake of air from outside in different quantities according to the needed granulometry to obtain.

The above technical problem is solved by a nebulization device for medical mixture, of the type comprising a containing ampoule for the medical mixture, at least one atomizer for the intake of pressurized gas within said ampoule, at least one emission opening of said nebulized medical mixture and at least one window for the intake of air from outside. The atomizer is surmounted by an upper portion of the ampoule. At least one, preferably two selection side windows are further provided on the wall of the upper portion of the ampoule, whose opening is shielded by shielding means. Said shielding means are moved, precisely allowing the shielding, by a command shaft thereto connected and by a shielding selector coupled and linked to a control knob connected to said command shaft; the coupling between said control shaft and said shielding selector being obtained by a threaded coupling.

According to a preferred embodiment, the shielding means are comprised in a skirt-shaped shielding selector which the shaft is connected to.

Furthermore, according to a preferred embodiment, the command shaft extends along the central axis of the duct.

According to another aspect of the invention, the shielding means consist in at least two bulkheads which extend parallel to the command shaft at the selection side windows.

According to another aspect of the invention, the nebulization device further comprises a control knob at an end of the command shaft in order to vary the position along the axis of the shaft itself through a rotary-translational movement.

According to a further aspect of the invention, the rotary-translational movement of said control knob that moves the command shaft is obtained through a cam groove obtained on an inner wall of the ampoule within which the control knob moves.

Alternatively, according to another embodiment of the invention, a wide-radius external thread is provided on the outer surface of the command shaft, external thread that engages with a corresponding inner thread of a threaded portion of the shielding selector.

According to a second embodiment of the present invention, the shielding selector comprises two additional entry windows for the intake of air within said ampoule.

According to a further aspect of the invention, the nebulization device further comprises at least two valves at a base of said control knob for the variation of air flow into the inhalation and exhalation phases.

Still according to another aspect of the present invention, the nebulization device provides a mouthpiece at the emission outlet for the connection with the patient's air tracts.

Furthermore, according to an aspect of the invention, the ampoule is made of two pieces interconnected to each other.

Further features and advantages will become clearer from the following detailed description of a preferred, but not exclusive, embodiment of the present invention, with reference to the appended figures given by way of non-limiting example.

BRIEF DESCRIPTION OF THE DRAWINGS

In said drawings:

FIGS. 2a, 2b and 2c represent sectional views of the three operating positions of the nebulization device of FIG. 1;

DETAILED DESCRIPTION

Figure 1:
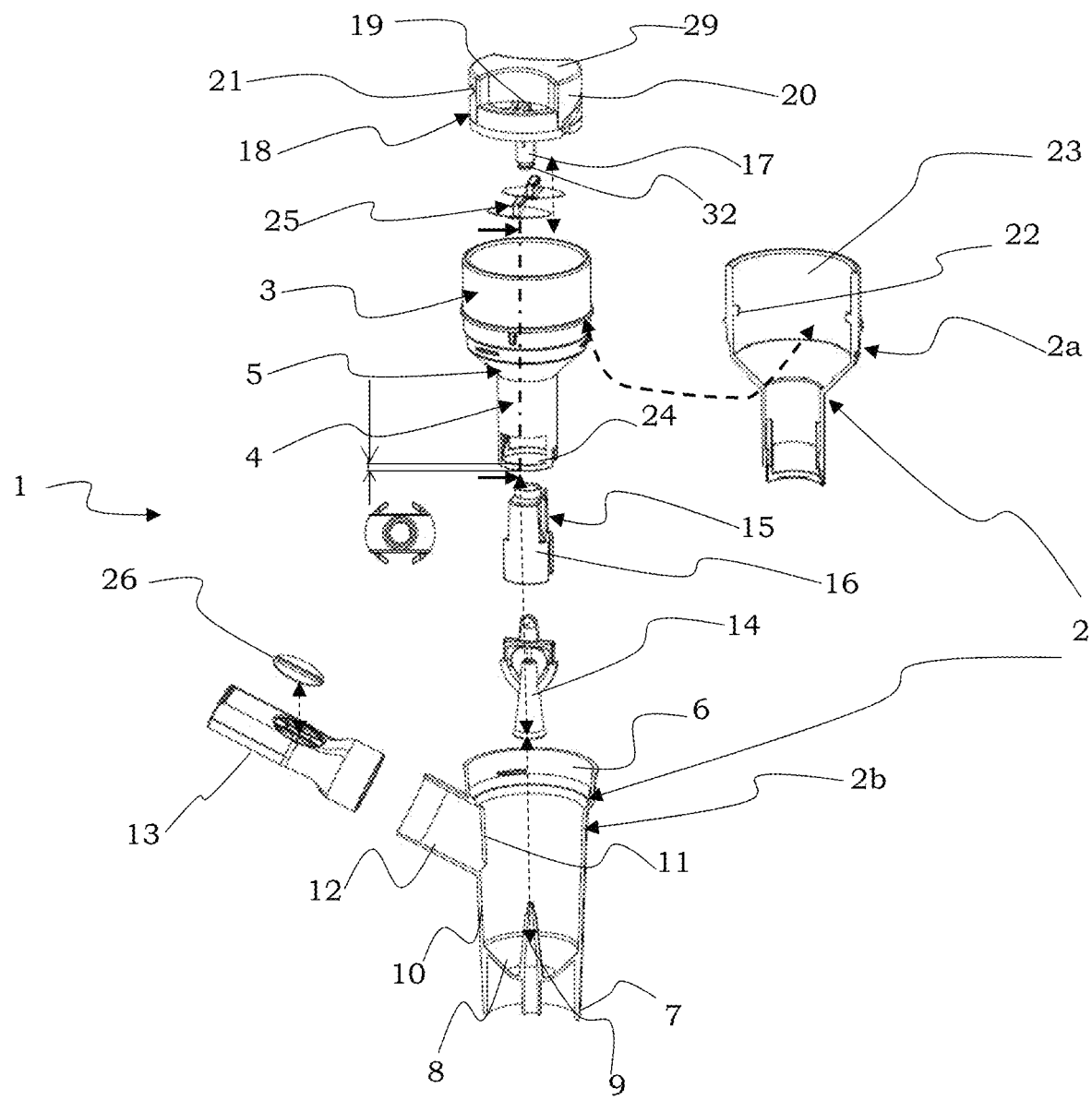
FIG. 1 represents an exploded view of an embodiment of the nebulization device according to the invention.

With reference to the figures, and particularly to FIG. 1, reference number 1 globally and schematically indicates a nebulization device realized according to the present invention.

Said nebulization device 1 is illustrated in the Figures arranged vertically, according to a preferred operating configuration. In the following of the present invention, the positions and orientations, relative and absolute, of the various elements which the device is made of, defined by means of terms such as upper and lower, on and under, horizontal and vertical or other equivalent terms, will be expressed with reference to said configuration without them representing a limitation of the Applicant's rights.

The nebulization device 1 comprises an ampoule 2, preferably divided into two components, an upper component 2a and a lower component 2b, respectively.

The upper component 2a is preferably shaped as a circular section with an upper portion 3, having a larger diameter, and a lower portion 4, having a smaller diameter, which are connected to each other by a truncated-conical portion 5.

The lower component 2b preferably is also shaped as a circular section. Said lower component 2b preferably has an ergonomic profile externally, which facilitates the grip by the patient during the therapy. The lower component 2b further has an open end 6 within which the coupling with the upper component 2a occurs.

Preferably, at a side surface 10 of the component 2b, there is an opening 11 from which a duct segment 12 departs, which is preferably inclined by an angle with respect to a cross-section of the lower component 2b.

The duct segment 12 is shaped so as to couple to a connection device with the patient's air tracts, such as, for instance, a mouthpiece 13.

Nothing forbids adopting other connection devices with the patient's air tracts, such as the known nasal masks or forks.

At an end 7 opposite the open end 6, there is a closing surface 8, which is glass-shaped and comprising a nozzle-duct 9.

On the nozzle-duct 9 an atomizer 14 (also known in the art with the name of "pisper") is fitted.

Said atomizer 14 is surmounted by the lower portion 4 of the upper component 2a.

Between such a lower portion 4 and the atomizer 14 a shielding selector 15, which is preferably skirt-shaped, comprising at least one, preferably two, shielding means 16, is interposed. Said shielding means preferably consist in two bulkheads that develop parallel according to the longitudinal development of the ampoule 2. Furthermore, said shielding means 16 are preferably circumference-arc shaped.

Differently from the prior art, the invention does not provide any movement of the duct for the intake of air within the nebulization device to vary the relative position thereof with respect to the atomizer from which the intake of pressurized gas occurs, but just a relative movement of the shielding means 16 with respect to the atomizer 14.

The shielding means 16, according to the position along the axis, can control the flow coming from the atomizer 14. The shielding selector 15 is connected at an end 32 of the command shaft 17 which controls the movement thereof.

The command shaft 17, preferably provided along the longitudinal transversal axis of the ampoule 2, slides longitudinally, precisely moving the shielding selector 15.

At the opposite end 33 of the command shaft 17 and connected thereto a control knob 18 is preferably provided.

It is possible to provide for the control knob 18 to be integrally formed with the command shaft 17.

The shielding selector 15 is coupled and linked to the control knob 18 connected to said command shaft 17; the coupling between said command shaft 17 and said shielding selector 15 being obtained by a threaded coupling; for instance, a worm screw coupling.

The control knob 18 has a circular section, with a gripping portion 29 along a diameter thereof, ergonomically shaped to facilitate the rotation of the control knob 18.

The control knob 18, at the sides of the gripping portion 29, is crossed by at least one, preferably two entry windows 19, through which there is the intake of external air within the ampoule 2.

The control knob 18 provides a cam groove 21 on the outer surface 20.

The cam groove 21 is engaged by corresponding engaging pins 22 arranged at an inner surface 23 of the upper portion 3 of the upper component 2a.

At the lower portion 4 of the upper component 2a, at least one, preferably two, selection side windows 24 are obtained. Below said selection side windows 24 there is a lower portion sector 4 having height H. The two windows 24 are preferably provided on diametrically opposite parts.

Said selection side windows 24 can be totally, partially or not at all obstructed by the shielding means 16, as it can be seen in FIGS. 2a, 2b and 2c, respectively.

Immediately contiguous to the control knob 18, at the entry windows 19, a valve system 25 is provided.

Figure 3C:
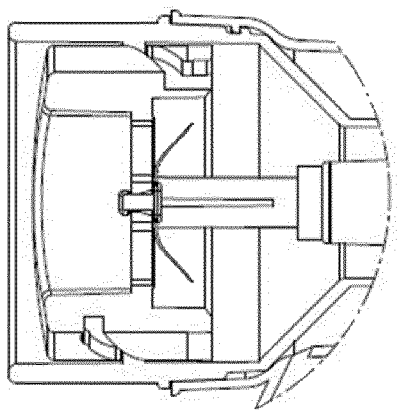
FIGS. 3a, 3b, 3c and 3d represent sectional views of the valve system and of the nozzle of the nebulization device of FIG. 1.
Figure 3B:
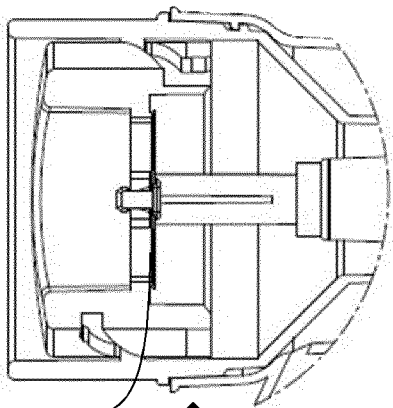
Figure 3D:
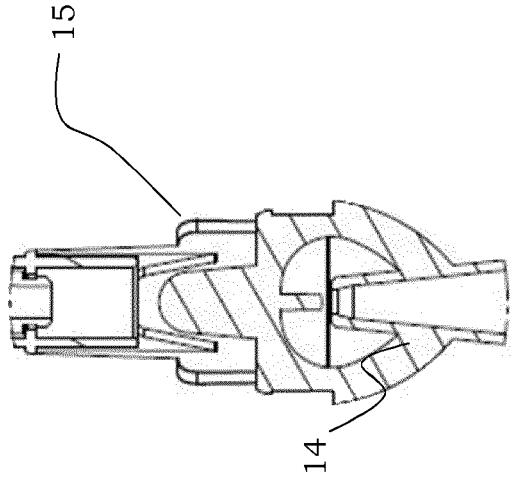
Figure 3A:
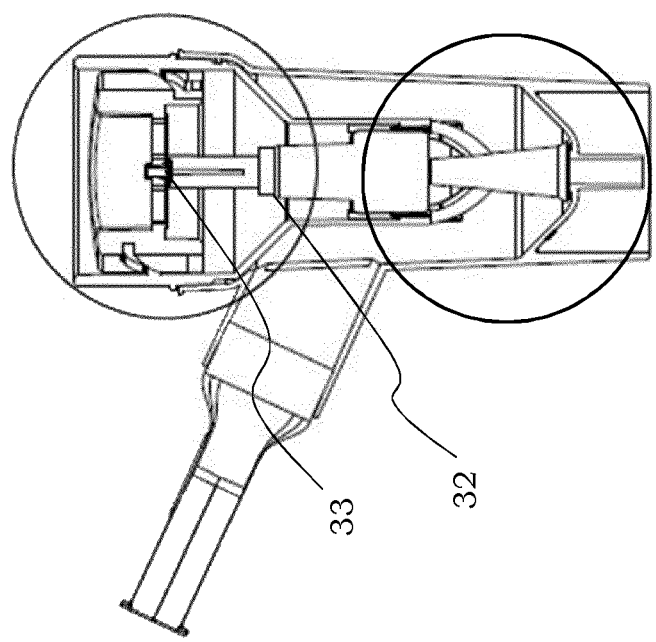

The valve system can be more evident in FIGS. 3a, 3b and 3c.

The valve system 25 works synergistically with a valve 26 present on the mouthpiece 13.

In particular, in FIGS. 3b and 3c respectively, the closing and opening conditions of the valve system 25 are represented.

The valve system 25 of the present embodiment comprises two valves which open in the inhalation phase. In this phase, on the contrary, the closing of the valve 26 arranged on the mouthpiece 13 occurs. Vice versa, in the exhalation phase the closing of the valves of the valve system 25 and the opening of the valve 26 on the mouthpiece 13 occur.

Instead, in FIG. 3d an enlarged section of the functional coupling between the nozzle duct 9, the atomizer 14 and the shielding selector 15 is highlighted.

Figure 4:
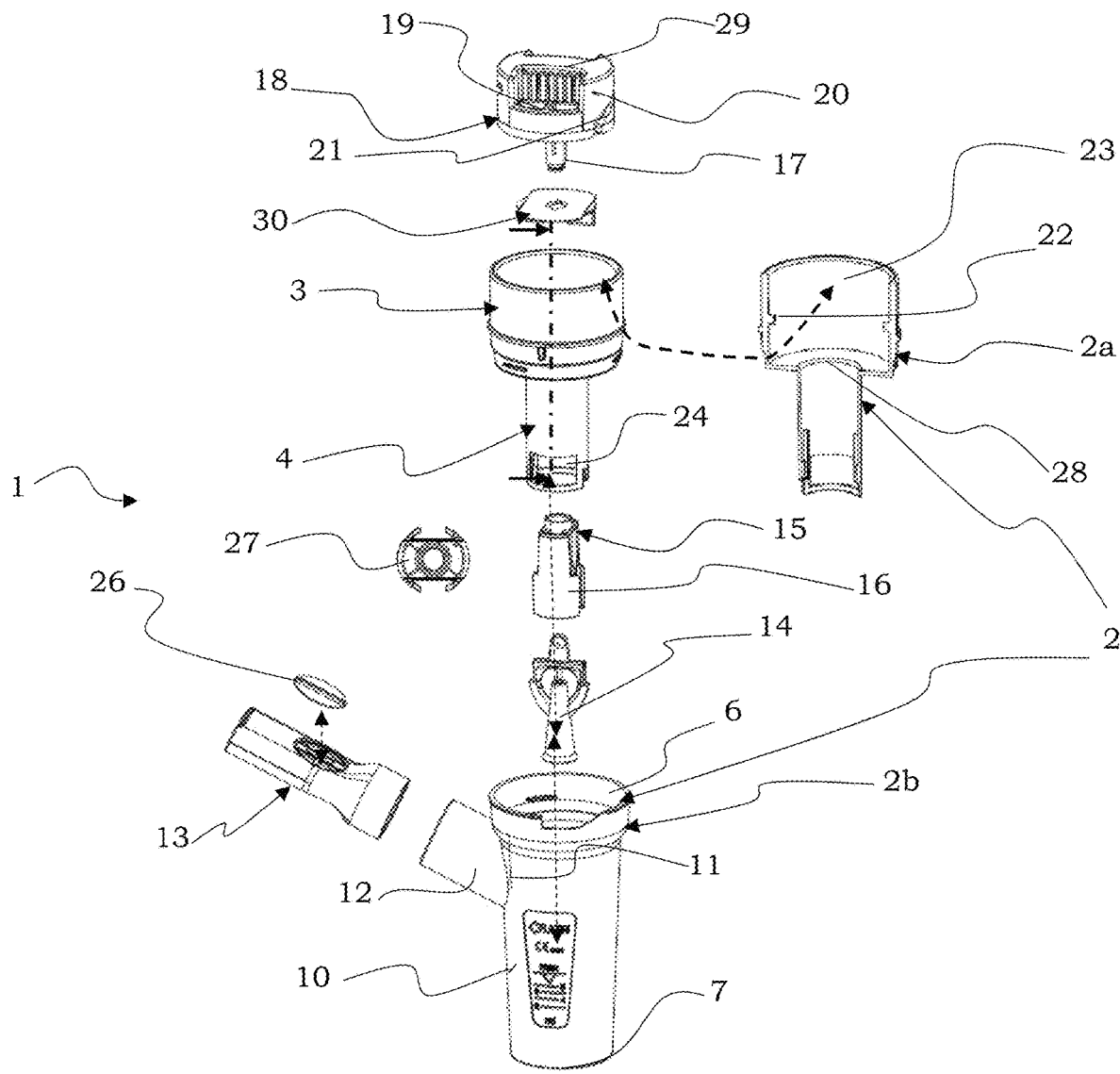
FIG. 4 represents an exploded view of a second embodiment of the nebulization device according to the invention.

In FIG. 4 a second embodiment of the present invention is represented.

Said embodiment differs from the embodiment represented in FIG. 1 in the presence of two additional entry windows 27 on the shielding selector 15, close to the coupling with the command shaft 17.

Another difference of this embodiment with respect to the embodiment of FIG. 1 is represented by the absence of the truncated-conical portion 5 between the upper portion 3 and the lower portion 4 of the upper component 2a of the ampoule 2. Instead of this truncated-conical portion 5, an immediate reduction in section between the upper portion 3 and the lower portion 4 is provided at a cross-section 28.

The lower portion 4 of the upper component 2a of the ampoule 2 is therefore longer with respect to the first embodiment of the invention.

A further difference of this embodiment with respect to the one represented in FIG. 1 is represented by the valve system 25. In fact, instead of the two valves of the first embodiment, a unique baffle 30 is provided.

Figure 6C:
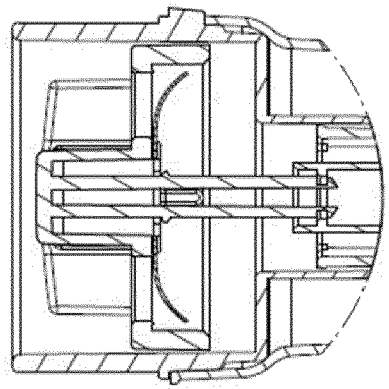
FIGS. 6a, 6b, 6c and 6d represent sectional views of the valve system and of the nozzle of the nebulization device of FIG. 1.
Figure 6B:
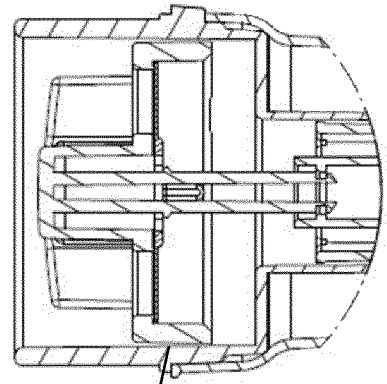
Figure 6D:
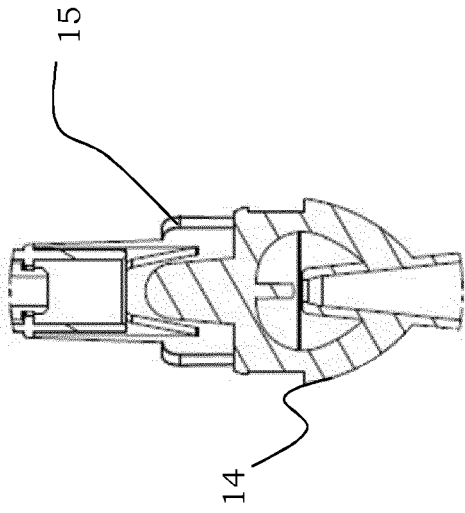
Figure 6A:
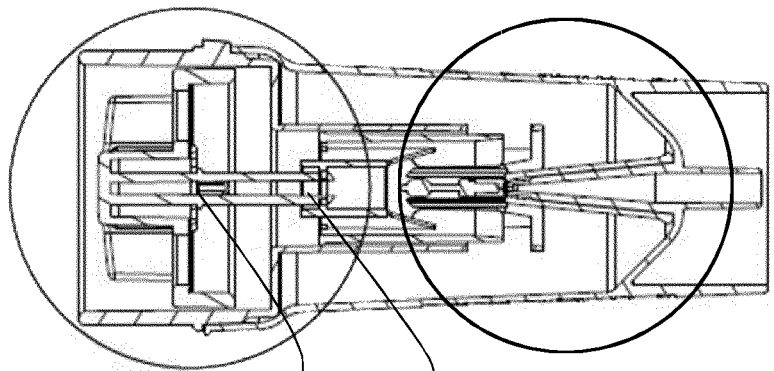

It is possible to see in detail the different valve system of the second embodiment in FIGS. 6a, 6b and 6c.

The baffle 30 operates analogously to the valves of the first embodiment. In fact, a deformation thereof inwards allows the air flow in the inhalation phase, when the corresponding valve 26 on the mouthpiece 13 is closed. Instead, in the exhalation phase the baffle 30 returns to a rectilinear conformation, thus occluding the entry windows 19, whereas the opening of the valve 26 occurs on the mouthpiece 13.

Instead, in FIG. 6d an enlarged section of the functional coupling between the nozzle duct 9, the atomizer 14 and the shielding selector 15 is highlighted.

Figure 7B:
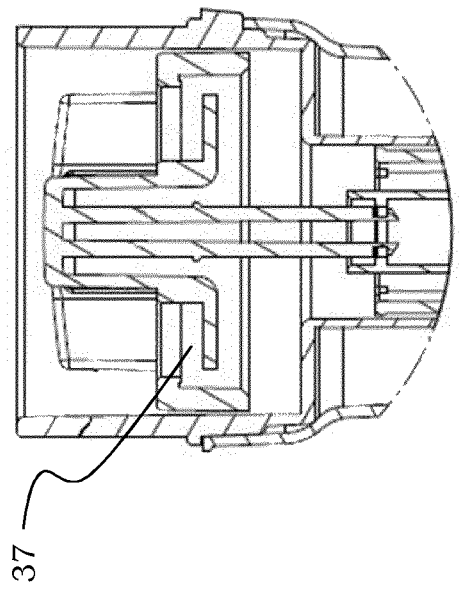
FIGS. 7a and 7b show the sectional views of a third embodiment of a nebulization device according to the invention.
Figure 7A:
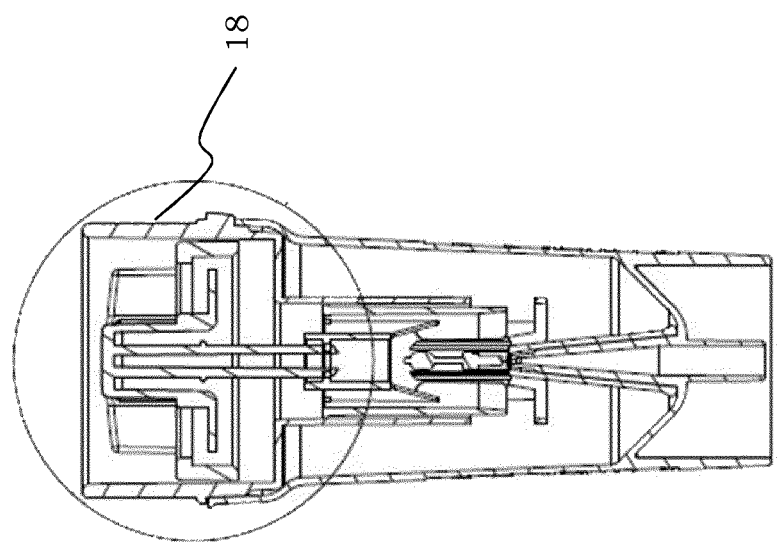
Figure 8B:
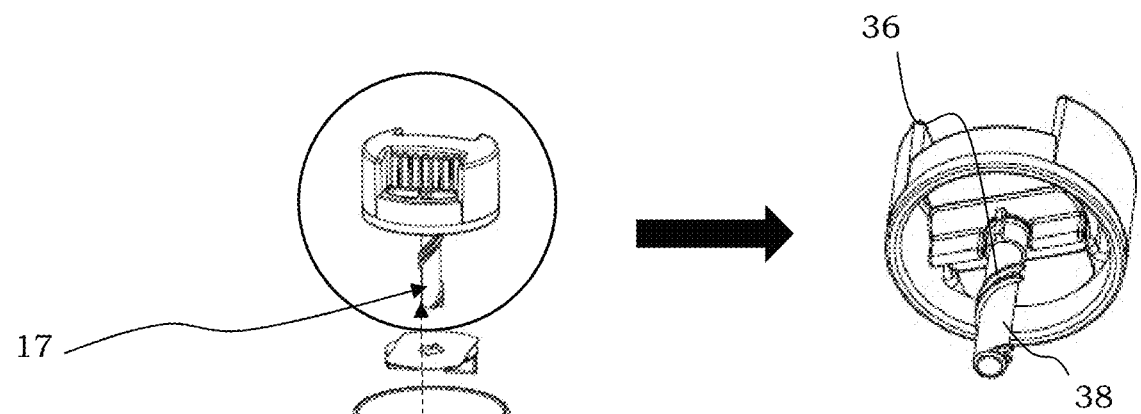
FIGS. 8a, 8b and 8c show an exploded view of a fourth embodiment of a nebulization device according to the invention.
Figure 8C:
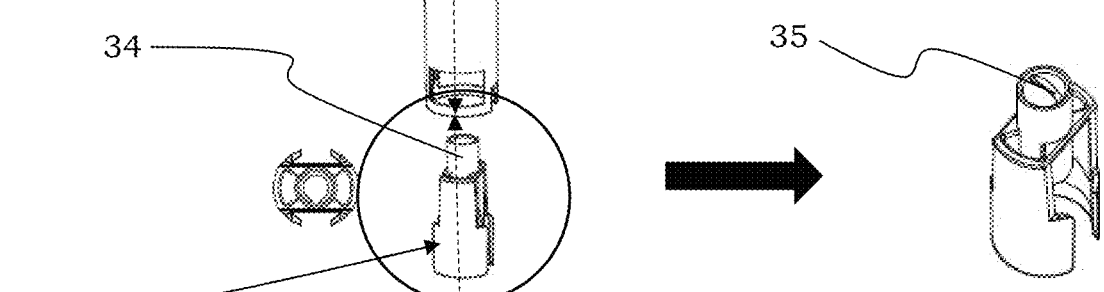
Figure 8A:
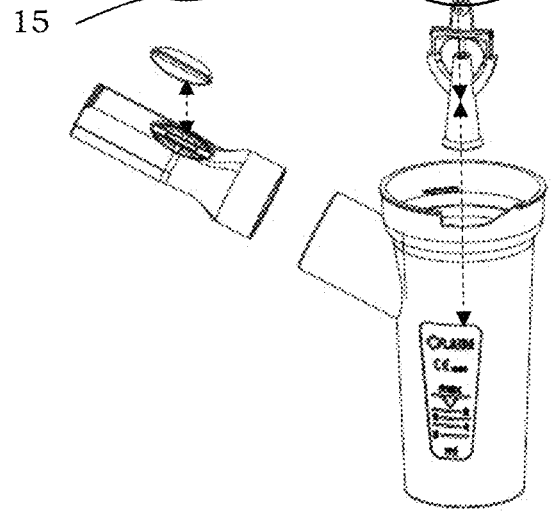

Since the valve system 25 is particularly complex and, consequently expensive, a third embodiment represented in FIGS. 7a and 7b is provided.

In said Figures it can be noticed that the valve system is replaced by a virtual valve system 37. Said virtual valve system 37 is obtained through a different conformation of the entry windows 19. In fact, instead of housing valves, such entry windows 19 have a "wolf-mouth" section, which is sufficient to ensure the correct delivery of the nebulized and meanwhile to properly obstruct the discharge of the flow exhaled by the patient. In this way said exhaled flow is free to vent through the side windows of the mouthpiece, which is also devoid of a valve.

A fourth embodiment is also provided, which is realized as an alternative adjustment mode through the shielding selector 15.

According to said embodiment, the shielding selector 15 is provided with a threaded portion 34 protruding upwards, which is provided with an inner thread 35, which is at least a single-start-thread.

Said inner thread 35 is engaged by at least one wide-radius external thread 36 obtained on an external surface 38 of the command shaft 17.

As a result, the above-mentioned adjustment of the shielding selector 15 is obtained through a rotary movement of the command shaft 17 within the threaded portion 34 of the shielding selector 15 itself.

Therefore, engaging pins 22 sliding in a cam groove 21 of the control knob 18 are not provided.

Said solution allows reducing the size in height both of the control knob 18 and of the upper part 2a, thus making the ampoule 2 more compact.

Figures 9A, 9B:
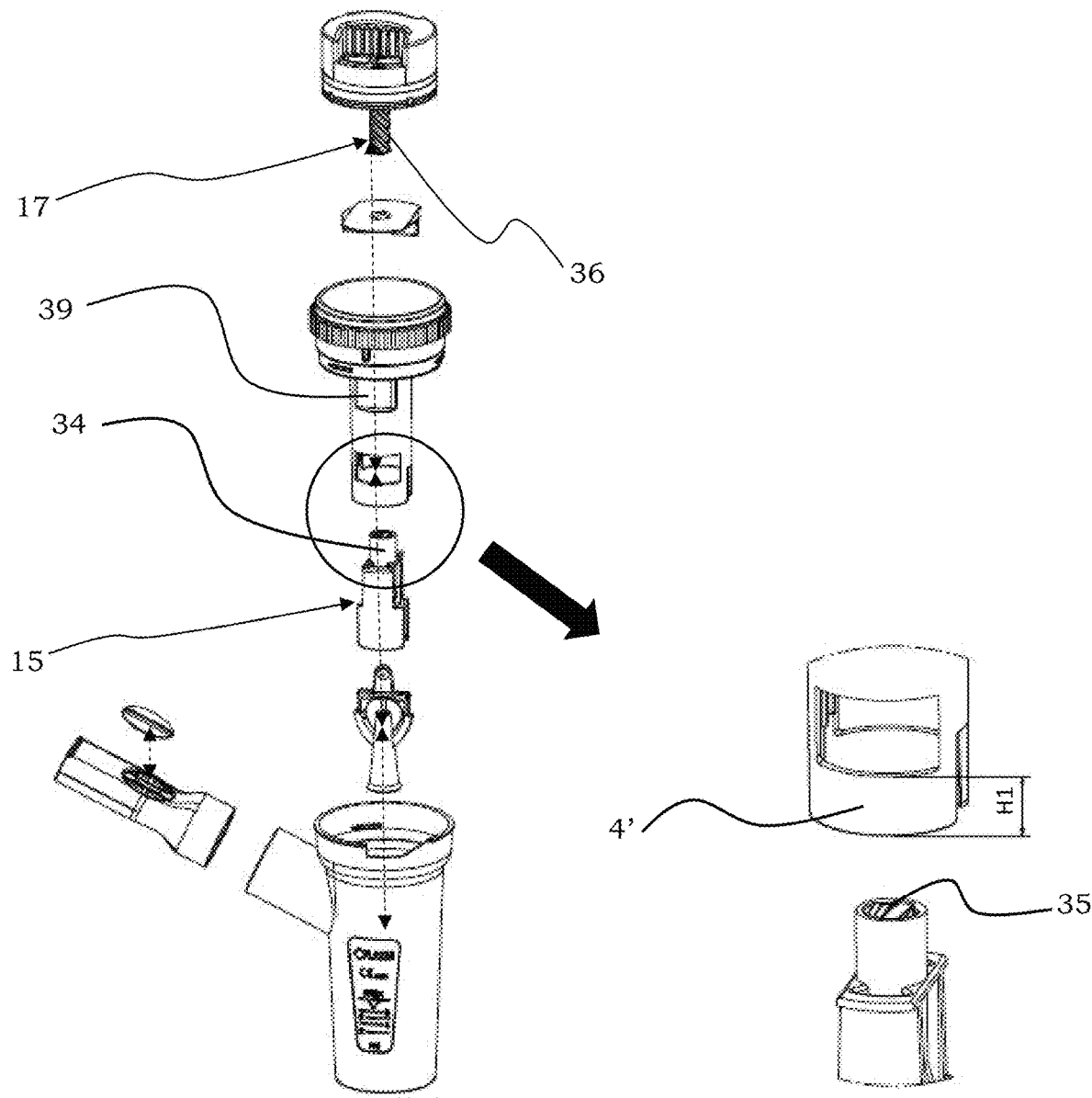
FIGS. 9a, 9b show an exploded view of a variant of the embodiment of FIGS. 8a, 8b and 8c.

Nothing forbids using a threaded coupling with a multiple-start thread 36 as represented in FIGS. 9a, 9b instead of a wide-radius external thread 36 with an almost similar operation.

In said Figures a lower portion sector 4' is further shown, below the selection side windows 24, having height H1, which is greater than the dimension H present in the described embodiments. Said dimension variation allows both strengthening such a sector and obtaining a better selection of the size of the particles, which can have more reduced size.

Furthermore, the protuberance 39 houses locking wings adapted to block the rotation of the command shaft 17 within the threaded portion 34 of the shielding selector 15 once the desired shielding position has been reached.

In the following the operation of the nebulization device 1 according to the invention will be described, considering, for illustrative purpose, the above described embodiments.

Figure 5A:
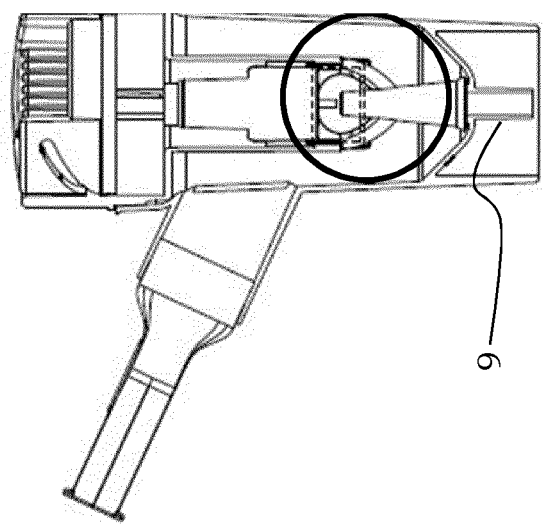
FIGS. 5a, 5b and 5c represent sectional views of the three operating positions of the nebulization device of FIG. 4.
Figure 5B:
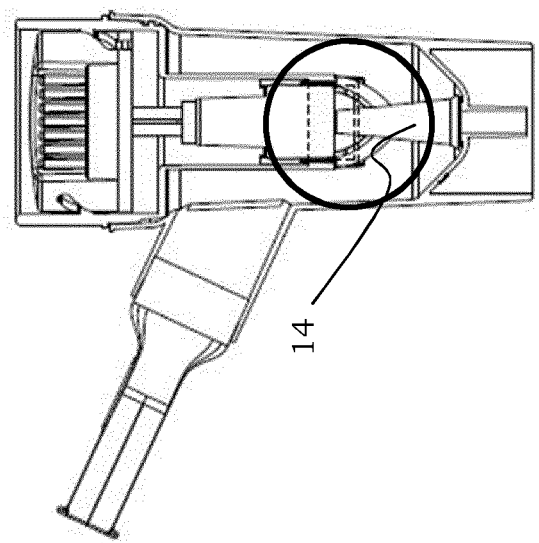
Figure 5C:
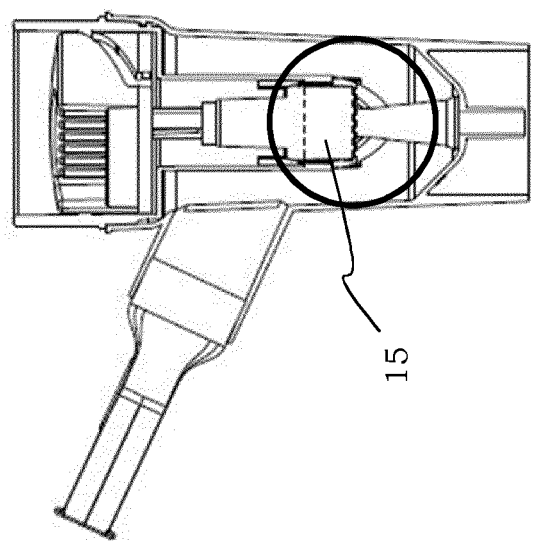

In particular, reference is made to FIGS. 2a, 2b and 2c for the first embodiment and to FIGS. 5a, 5b and 5c for the second embodiment.

Once the ampoule 2 of the nebulization device 1 has been filled in with medical fluid and assembled, the operation of the components also present in the prior art does not result to be varied.

Therefore, the intake of pressurized gas through the nozzle duct 9 and the atomizer 14 occurs.

Simultaneously, through the entry windows 19 the intake of external air within the ampoule 2 occurs.

Therefore, the nebulization of the medical fluid occurs, which is inhaled by the patient through the mouthpiece 13 connected to the emission duct 12.

According to the invention, through the command shaft 17, the shielding selector 15 and the selection side windows 24 the required granulometry can be obtained.

Through the rotation of the control knob 18 and the consequent sliding of the engaging pins 22 within the cam groove 21, there occurs a rotary-translational movement of the control knob and jointly of the command shaft 17.

Thus, the movement of the shielding selector 15 and of the shielding means 16 is thus allowed.

As seen, the present embodiments provide three selection positions, to each of which the correct granulometry for the respiratory tract affected by the specific patient's therapy corresponds.

This does not exclude that it is possible to provide a greater number of positions to specify even more a tract to which a therapy can be addressed, without departing from the object of the present invention defined by the appended claims.

The three illustrated selection positions correspond, in this case, to:
- position 1, as illustrated in FIGS. 2a, 5a: a total opening of the selection side windows 24 by the shielding means 16 of the shielding selector 15;
- position 2, as illustrated in FIGS. 2b, 5b: a partial opening of the selection side windows 24 by the shielding means 16 of the shielding selector 15;
- position 3, as illustrated in FIGS. 2c, 5c: a total occlusion of the selection side windows 24 by the shielding means 16 of the shielding selector 15.

In this way, there are obtained, respectively:
large particles for the treatment of the upper respiratory tracts;
particles suitable for the tracheo-bronchial tract treatment;
fine particles for the treatment of pulmonary alveoli.

In particular, experiments performed by the Applicant have shown that the ampoule 2, according to the configuration, allows obtaining a dimensional difference of MMAD (Mass Median Aerodynamic Diameter) of the particles which varies:
by about 30-50% between position 1 and position 2, and by about 150-200% between position 1 and position 3.

Surely, the delivery speeds also differ markedly, indicatively by the same variation value cited for the dimensions of the particles.

Using the second embodiment illustrated in FIG. 4 and previously described, through the use of the additional entry windows 27 on the shielding selector 15, the flow area for the air entering the ampoule 2 is varied.

Clearly, the greater or smaller dimension of the flow area and therefore the greater or lesser consistency of the air flow affects both the delivery speed and the size of the aerosol particles generated by the ampoule 2.

Furthermore, in the second embodiment illustrated in FIG. 4, the replacement of the truncated-conical portion 5 instead of a sharp reduction in diameter between the upper portion 3 and the lower portion 4 of the upper component 2a may also affect the performance of the ampoule 2.

Advantageously, the described nebulization device allows the formation of a medical aerosol having different granulometries. In this way the nebulization device 1 according to the invention allows being universally optimized for all the required therapies, whether they are directed to the upper respiratory tracts, to the tracheo-bronchial tract, or more internally to the pulmonary alveoli.

Further advantageously, this can be simply obtained by rotating a control knob 18 by a predetermined quantity, thus reaching the correct level of shielding of the flow exiting from the atomizer 14.

Furthermore, advantageously, the nebulization device 1 is completely disassemblable. Therefore, the practicality of the cleaning, disinfection and sterilization phases of the nebulization device 1 components is improved. In fact, with respect to the prior art, embedded, hidden or difficult to reach components are not present, as above described. In this way the hygiene required for a medical device and the prevention of the proliferation of germs, bacteria and viruses are ensured.

Still advantageously, the disassemblability feature is inherently connected to the substitutability feature. It is in fact possible, in case of malfunction or damage to one of the components, to only replace the malfunctioning or damaged component.

A skilled person will also understand how the nebulization device 1 according to the invention is practical to use by any patient, without the possibility to incur errors which could make the therapy ineffective.

Still advantageously, the components of the nebulization device 1 are made of materials suitable for the purpose, both in terms of nebulization and in terms of strength, easy availability and lastly, they are not overly expensive.

The skilled person will understand that the embodiment described can be subjected to various changes and variations, according to specific and contingent needs, all included within the scope of protection of the invention, as defined by the following claims.

What is claimed is:
1. A nebulization device for medical mixture comprising:
a containing ampoule for said medical mixture, comprising an upper component and a lower component connected to each other;
at least one emission opening of said medical mixture from said ampoule, and
at least one entry window for an intake of air within said ampoule;
at least one atomizer for the intake of pressurized gas, within said lower component of said ampoule, said atomizer being surmounted by said upper component,
at least one selection side window on said upper component, an opening of said selection side window being shielded by shielding means;

wherein the shielding means are moved by a command shaft through a shielding selector coupled and linked to a control knob connected to said command shaft;

a coupling between said command shaft and said shielding selector being obtained by a threaded coupling.

2. The nebulization device according to claim 1, wherein the shielding selector is a skirt shaped shielding selector and said command shaft is connected at one end of the skirt shaped shielding selector comprising said shielding means.

3. The nebulization device according to claim 1, wherein said command shaft extends along a central axis of said upper component.

4. The nebulization device according to claim 1, wherein said shielding means comprise of at least two bulkheads which develop parallel to a longitudinal extension of said ampoule, at said selection side window.

5. The nebulization device according to claim 1, wherein said shielding selector further comprises two additional entry windows for the intake of air within said ampoule.

6. The nebulization device according to claim 1, wherein said control knob placed at one end of said command shaft opposite to said shielding selector varies the vertical position of said command shaft through a rotary-translational movement.

7. The nebulization device according to claim 1, wherein said control knob provides a cam groove at an outer surface thereof, which is coupled to corresponding engaging pins at an inner surface of said upper component.

8. The nebulization device according to claim 1, further comprising at least one valve system at a base of said control knob for a flow variation of air flow during a user's inhalation and exhalation phases.

9. The nebulization device according to claim 1, comprising providing a virtual valve system wherein said at least one entry window is wolf-mouth-shaped for adjusting an air flow entering and exiting from said ampoule during a user's inhalation and exhalation phases.

10. The nebulization device according to claim 1, wherein said shielding selector comprises a threaded portion protruding upward, the threaded portion comprising an inner thread, the inner thread being engaged by at least one wide-radius external thread obtained on an external surface of said command shaft, to shield the opening of said at least one selection side window.

11. The nebulization device according to claim 10, further comprising rotation locking wings for said command shaft within said threaded portion.

12. The nebulization device according to claim 1, further comprising a duct segment for a coupling with a mouthpiece at said at least one emission opening.

13. The nebulization device according to claim 1, wherein said at least one selection side window comprises two selection side windows.

* * * * *